United States Patent [19]

Klaenhammer et al.

[11] Patent Number: 5,139,950
[45] Date of Patent: Aug. 18, 1992

[54] PTR2030, A CONJUGAL PLASMID AND DERIVATIVES THEREOF THAT CONFER PHAGE RESISTANCE TO GROUP N STREPTOCOCCI

[75] Inventors: Todd R. Klaenhammer; Rosemary B. Sanozky, both of Raleigh, N.C.; Larry R. Steenson, West Lafayette, Ind.

[73] Assignee: North Carolina State University, Raleigh, N.C.

[21] Appl. No.: 532,027

[22] Filed: Jun. 1, 1990

Related U.S. Application Data

[60] Division of Ser. No. 256,018, Oct. 11, 1988, Pat. No. 4,931,396, which is a continuation-in-part of Ser. No. 748,444, Jun. 25, 1985, abandoned.

[51] Int. Cl.$^5$ .................. C12N 1/21; C12N 15/75; C12N 15/00; A23C 9/12
[52] U.S. Cl. .................. 435/252.3; 435/253.4; 435/320.1; 435/885; 435/172.3; 426/61; 935/59
[58] Field of Search ............... 435/172.3, 252.3, 253.4, 435/320.1, 885, 853, 252.9; 935/29; 426/61

[56] References Cited

U.S. PATENT DOCUMENTS

| | | | |
|---|---|---|---|
| 4,332,892 | 6/1982 | Ptashne et al. | 435/69.1 |
| 4,418,149 | 11/1983 | Ptashne et al. | 435/252.33 |
| 4,530,904 | 7/1985 | Hershberger et al. | 435/172.3 |

OTHER PUBLICATIONS

M. Casadaban et al., "β-Galactosidase Gene Fusions for Analyzing Gene Expression in *Escherichia coli* and Yeast," *Methods in Enzymology* 100, 293-308 (1983).
A. Chopin et al., "Two Plasmid-Determined Restriction and Modification Systems in *Streptococcus lactis*," *Plasmid* 11, 260-263 (1984).
W. De Vos, "Plasmid DNA in Lactic Streptococci: Bacteriophage Resistance and Proteinase Plasmids in Streptococcus Cremoris SK11," *Chemical Abstracts* 105, 3 (Abstract No. 19507d) (1986).
M. Gething and J. Sambrook, "Construction of Influenza Haemagglutinin Genes that Code for Intracellular and Secreted Forms of the Protein," *Nature* 300, 598-603 (1982).
C. Gonzalez and B. Kunka, "Transfer of Sucrose-Fermenting Ability and Nisin Production Phenotype among Lactic Streptococci," *Applied and Environmental Microbiology* 49, No. 3, 627-633 (1985).
T. Klaenhammer and R. Sanozky, "Conjugal Transfer from *Streptococcus lactis* ME2 of Plasmids Encoding . . . ," *Journal of General Microbiology* 131, 1531-1541 (1985).
T. Klaenhammer, "Interactions of Bacteriophages with Lactic Streptococci," *Advances in Applied Microbiology* 30, 1-29 (1984).
L. McKay and K. Baldwin, "Conjugative 40-Megadalton Plasmid in *Streptococcus lactis* subsp. diacetylactis DRC3 is Association with . . . ," *Applied and Environmental Microbiology* 47, No. 1, 68-74 (1984).
T. Roberts and G. Lauer, "Maximizing Gene Expression on a Plasmid Using Recombination in Vitro," *Methods in Enzymology* 68, 473-483 (1979).
M. Sanders and T. Klaenhammer, "Phage Resistance in a Phage-Insensitive Strain of *Streptococcus lactis:* Temperature-Dependent Phage . . . ," *Applied and Environmental Microbiology* 47, No. 5, 979-985 (1984).
M. Sanders and T. Klaenhammer, "Characterization of Phage-Sensitive Mutants from a Phage-Insensitive Strain of *Streptococcus lactis:* Evidence . . . ," *Applied and Environmental Microbiology* 46, No. 5, 1125-1133 (1983).
M. Sanders and T. Klaenhammer, "Evidence for Plasmid Linkage of Restriction and Modification in *Streptococcus cremoris* KH," *Applied and Environmental Microbiology* 42, No. 6, 944-950 (1981).
M. Sanders and T. Klaenhammer, "Restriction and Modification in Group N Streptococci: Effect of Heat on Development of Modified Lytic Bacteriophage," *Applied and Environmental Microbiology* 40, No. 3, 500-506 (1980).

*Primary Examiner*—Richard A. Schwartz
*Assistant Examiner*—Richard M. Lebovitz
*Attorney, Agent, or Firm*—Bell, Seltzer, Park & Gibson

[57] ABSTRACT

The present invention relates to the plasmid pTR2030 and derivatives thereof which confer phage resistance to group N streptococci. The invention further relates to microorganisms containing pTR2030 or a derivative thereof and to starter cultures containing the microorganisms.

6 Claims, 1 Drawing Sheet

PTR2030, A CONJUGAL PLASMID AND DERIVATIVES THEREOF THAT CONFER PHAGE RESISTANCE TO GROUP N STREPTOCOCCI

This application is a division of application Ser. No. 07/256,018, now U.S. Pat. No. 4,931,396 filed Oct. 11, 1988, which is a continuation-in-part of prior application Ser. No. 06/748,444, filed Jun. 25, 1985, now abandoned.

BACKGROUND OF THE INVENTION

1. Field of the Invention

The present invention relates to the plasmid pTR2030 and to derivatives thereof. More specifically, the present invention relates to the plasmid pTR2030 which carries genetic determinants for phage resistance to group N streptococci and to derivatives of this plasmid which also carry the same genetic determinants.

2. Description of the Prior Art

Production of cheese and cultured dairy products has long relied on the fermentation of milk by group N streptococci. Members of this group, composed of *Streptococcus lactis, S. cremoris*, and *S. lactis* subsp. diacetylactis, are directly responsible for the acid development, flavor production, and often coagulum characteristics in mesophilic dairy fermentations. Because efficient milk fermentations are dependent on the growth and activity of the lactic streptococci, great care is exercised to prepare starter cultures that are highly active and uncontaminated with undesirable microorganisms or bacteriophages. However, the fermentation process itself is nonaseptic, occurring in open vats with a nonsterile medium, pasteurized milk. It is therefore highly susceptible to contamination with bacteriophages. For the majority of strains of lactic streptococci employed in commercial dairy fermentations, lytic bacteriophages capable of halting growth and acid production can appear within 1 to 2 days after introducing the culture into the cheese plant. Although bacteriophage contamination of numerous industrial fermentations has been observed, the destructive role of bacteriophages in milk fermentations is without parallel in other fermentation processes.

Historically, milk fermentations relied on starter cultures composed of undefined mixtures of lactic streptococci propagated without knowledge of, or protection from, bacteriophages. Natural phage contamination in these cultures established an equilibrium of evolving bacteriophages and phage-resistant variants. These cultures were highly variable in day-to-day levels of acid production, but remained moderately active and could be used continuously in small fermentation factories. Over the past 20 years, starter culture failures due to bacteriophage infection have become prevalent throughout the dairy industry. Increasing demand for cultured milk products in recent years has necessitated increases in both production capacity and process efficiency such that larger volumes of milk are processed, cheese vats are filled repeatedly within a single day, and total processing time is shortened. This modernization of the industry concurrently increased the probability of phage contamination and further dictated the use of defined mixtures of lactic streptococci capable of uniform and rapid rates of acid production. With the selection of highly fermentative lactic streptococci and their propagation under aseptic conditions (in the absence of bacteriophages), the majority of cultures now used by the industry have become highly susceptible to bacteriophage attack upon introduction into the cheese factory.

To cope with bacteriophage problems a number of successful methods have been developed to minimize phage action during commercial milk fermentations. Through the use of concentrated cultures, aseptic bulk starter vessels and phage-inhibitory media (see for example, U.S. Pat. No. 4,282,255), the starter culture can be protected from bacteriophage infection prior to vat inoculation. However, phage contamination cannot be prevented following entrance into the fermentation vat. Therefore, emphasis for protection of the culture shifts to minimizing prolific phage-host interactions through rotation of phage-unrelated strains or use of phage-resistant mutants in multiple-strain starters. Although, in theory, strain rotation should minimize developing phage populations within the plant, in practice it has proved difficult to identify strains that demonstrate completely different patterns of phage sensitivity. Estimates of the total number of different, phage-unrelated lactic streptococci approximate 25 strains worldwide. Considering the small number of phage-unrelated strains available, the choice of strains for incorporation into rotation programs is severely limited. Similarly, few phage-unrelated strains are available for construction of multiple-strain starters containing composites of 4 to 6 strains.

A decade ago, Sandine, W. E. et al., *J. Milk Food Technol.* 35, 176 (1972) emphasized the need to isolate new strains of lactic streptococci for use in the dairy industry. Foremost among the criteria for selection of these strains was resistance to existing bacteriophages. It is now recognized that some strains of lactic streptococci are not attacked by any phage when challenged with large collections of laboratory phage banks, or when used on a continuous, long-term basis in commercial fermentations. These reports demonstrate the existence of lactic streptococci that are not sensitive to bacteriophage attack, in spite of devastating phage pressure such as that which routinely occurs within the factory environment. However, to date, only a limited number of phage-insensitive strains have been identified and studied for mechanisms of phage resistance.

Several mechanisms of phage resistance in group N streptococci have been identified and appear to be plasmid-associated. McKay, L. L. et al., *Appl.Environ.Microbiol.* 47, 68 (1984) describe a 40 megadalton plasmid, pNP40, found in *S. lactis* subsp. diacetylactis DRC3. When the plasmid was conjugally transferred to *S. lactis* C2, transconjugants were isolated which were resistant to phage c2 at 21° C. and 32° C., but not at 37° C. It was found that the resistance to c2 was not due to an inhibition of phage adsorption or to a classical modification-restriction system, but was suggested to be a temperature-sensitive DNase. The authors concluded that the genetic determinant for this resistance was located on pNP40.

Sanders, M. E., et al., *Appl.Environ.Microbiol.* 47, 979 (1984) reported that *S. lactis* ME2 was insensitive to a variety of phages. The authors determined that this insensitivity was the result of several temperature-sensitive mechanisms including: (a) prevention of phage adsorption, (b) the modification-restriction system, and (c) suppression of phage development. The authors reported that the genetic determinants for some of the mechanisms may be found on plasmids, but that some appeared to be found on the chromosomes.

Sanders, M. E., et al., *Appl.Environ.Microbiol.* 46, 1125 (1983) disclose that *S. lactis* ME2 contains a plasmid, pME0030, which codes for a function that prevents phage adsorption. Sanders, M.E. et al., *Appl.Environ.Microbiol.* 42, 944 (1981) disclose that a 10 megadalton plasmid found in *S. cremoris* KH codes for a modification-restriction system which enables this strain to be resistant to phage c2.

Gonzalez, C. F. et al., *Appl.Environ.Microbiol.* 49, 627 (1985) reported that two transconjugants of two matings of *S. lactis* SLA 2.24 or SLA 3.15 and *S. lactis* subsp. diacetylactis SLA 3.10 or SLA 3.23, respectively, showed temperature-independent phage resistance which was not due to adsorption or restriction in phage growth. Physical evidence for plasmid involvement was not obtained.

The identification or creation of plasmids encoding phage resistance in group N streptococci is necessary in order to genetically engineer strains that meet industrial criteria for fermentative capabilites and long-term phage resistance. The present invention provides for a plasmid which confers phage resistance to group N streptococci. Group N streptococci containing the plasmid or a derivative thereof are useful for formulating starter cultures which can be used for the production of cheese and cultured dairy products.

SUMMARY OF THE INVENTION

The present invention comprises a plasmid or a derivative thereof which confers phage resistance to group N streptococci. The present invention also comprises group N streptococci containing the plasmid or derivative. The present invention further comprises starter cultures containing such streptococci.

More specifically, the present invention comprises the plasmid pTR2030 and derivatives thereof which confer phage resistance to group N streptococci. pTR2030 carries genetic determinants which imparts resistance to phage. Derivatives of pTR2030 are considered herein to mean any plasmid capable of replication, transcription and translation in group N streptococci which carries the phage resistance genetic determinants of pTR2030. The invention further comprises group N streptococci which contain the plasmid pTR2030 or derivatives thereof and starter cultures containing these group N streptococci. Preferred streptococci include strains of *S. lactis*, *S. lactis* subsp. diacetylactis, and *S. cremoris*.

DETAILED DESCRIPTION OF THE INVENTION

Figure 1:
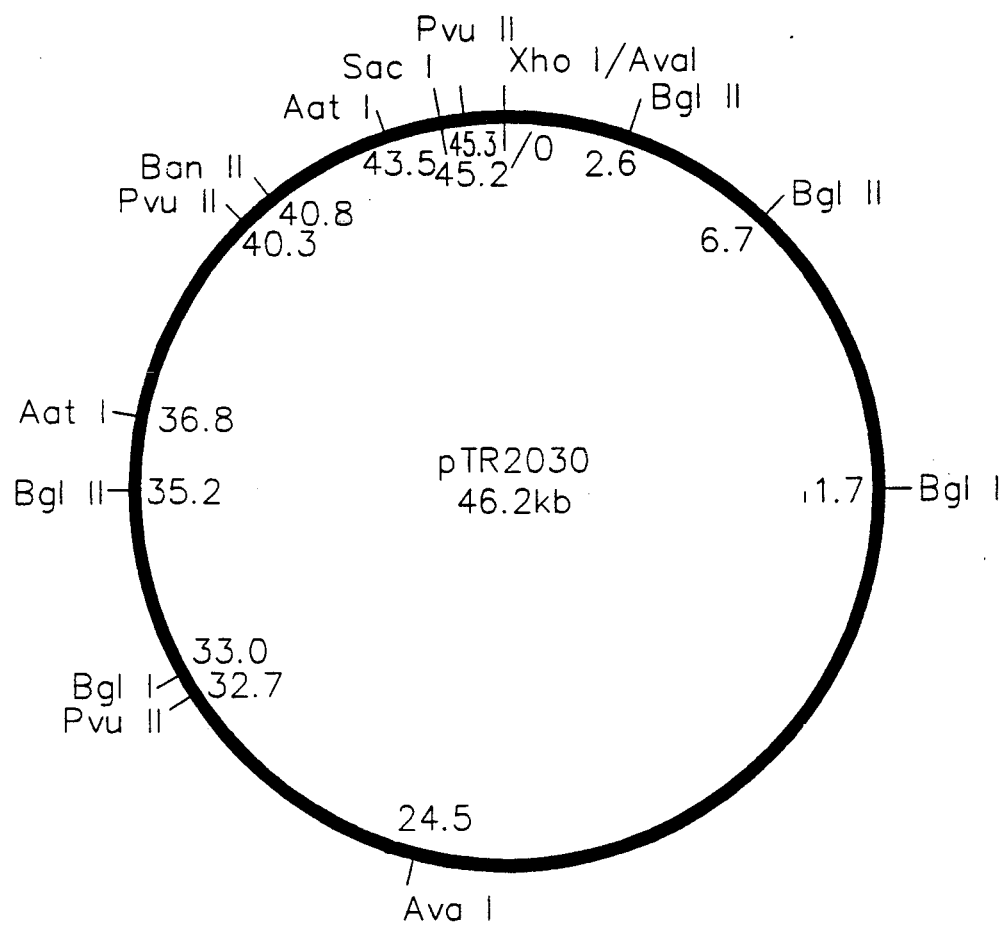
FIG. 1 illustrates a restriction map of pTR2030.

The present invention is directed to the plasmid pTR2030 and its derivatives which are useful for conferring phage resistance to group N streptococci. The latter are useful for formulating starter cultures for use in the production of cheese and cultured dairy products. pTR2030 and its derivatives could also be useful for conferring phage resistance to other gram-positive lactic acid bacteria used in dairy and food fermentation. pTR2030 carries genetic determinants which confer resistance to phage. The plasmid further carries genetic determinants for conjugal transfer. This genetic determinant promotes its own transfer as well as the transfer of other non-conjugative plasmids.

In order to provide a clear and consistent understanding of the specification and claims, including the scope given to such terms, the following definitions are provided:

Phage Resistance: Phage resistance is considered herein to mean a measurable inhibition of phage infection or proliferation. Inhibition of phage can be detected by changes in one or more of the following: efficiency of plaquing (EOP), plaque size, burst size, degree of cell lysis in broth, and level of acid production by cultures in a starter culture activity test in milk. Hsp+ and Hrp+ are used herein to describe the different types of phage resistance that may be displayed by different strains of Group N streptococci carrying pTR2030.

Derivative of pTR2030: A derivative of pTR2030 is used herein to refer to any plasmid capable of replication, transcription and translation in group N streptococci or other gram-positive lactic acid bacteria and capable of maintaining the phage resistance phenotype which is either (a) pTR2030 with inserted DNA sequences, or (b) pTR2030 with DNA sequences deleted, or (c) pTR2030 with inserted and deleted DNA sequences, or (d) a plasmid with a significant portion of a pTR2030 genetic determinant for phage resistance inserted therein.

Plasmid pTR2030 was isolated from a transconjugant of a mating of *S. lactis* ME2 and *S. lactis* LM0230. pTR2030 has a molecular weight of $30 \times 10^6$ daltons $\pm 10\%$. This corresponds to about 45 kilobases. pTR2030 appears to have been formed by a recombinational event as a result of the conjugal process. pTR2030 is distinct from plasmid pME0030, a 30 megadalton plasmid of *S. lactis* ME2 as evident from the available phenotypic evidence. First, it has been demonstrated that phage resistance (Hsp+) and conjugal transfer (Tra+), associated herein with pTR2030, are exhibited by *S. lactis* N1, a derivative of *S. lactis* ME2 which is cured of pME0030 (Sanders, M. E. et al., (1983), supra, and Sanders, M. E. et al. (1984), supra). pTR2030 encodes both Hsp+ and Tra+. Second, where the presence of pME0030 inhibits the adsorption of phage 18 to *S. lactis* ME2, the presence of pTR2030 in *S. lactis* LM0230 shows no effect on the adsorption of phage c2 or phage 18 (99% adsorption for both phages). Third, conjugation frequencies of Lac+, Nis$^r$, and phage resistance (Hsp+/Hrp+) occur at frequencies of $10^{-1}$/donor cell from transconjugants carrying pTR2030 as compared to frequencies of $10^{-6}$/donor cell from *S. lactis* ME2 carrying pME0030. Once formed, pTR2030 exhibits high frequency transfer ($10^{-1}$) in second round matings. The high-frequency conjugal ability of pTR2030 facilitates its use in genetic programs designed to introduce the plasmid into starter cultures that are sensitive to phage.

Table 1 shows the sensitivities of pTR2030 to several restriction endonucleases. The sizes of the fragments produced are also shown in Table 1. Tables 2 and 3 show an additional restriction analysis of pTR2030 and the map positions of restriction sites of pTR2030, respectively. FIG. 1 illustrates a restriction map of pTR2030.

TABLE 1

| | Restriction Enzyme | | | | | | |
|---|---|---|---|---|---|---|---|
| | HindIII | HaeIII | EcoRI | XbaI | HpaI | NcoI | AvaI |
| # of fragments* | 16 | 4 | 8 | 5 | 3 | 5 | 2 |

TABLE 1-continued

| | Restriction Enzyme | | | | | | |
|---|---|---|---|---|---|---|---|
| | HindIII | HaeIII | EcoRI | XbaI | HpaI | NcoI | AvaI |
| Sizes (Md) | 4.4 | 15.8 | 16.7 | 17.2 | 15.9 | 14.7 | 15.9 |
| | 3.0 | 3.9 | 7.8 | 5.3 | 12.1 | 13.0 | 14.4 |
| | 2.8 | 3.6 | 1.4 | 3.4 | 2.6 | 1.9 | |
| | 2.1 | 3.3 | 1.2 | 1.4 | | 1.2 | |
| | 2.0 | | 1.0 | 1.0 | | 0.8 | |
| | 1.9 | | 0.7 | | | | |
| | 1.6 | | 0.5 | | | | |
| | 1.3 | | 0.4 | | | | |
| | 1.2 | | | | | | |
| | 1.0 | | | | | | |
| | 0.9 | | | | | | |
| | 0.8~ | | | | | | |
| | 0.8~ | | | | | | |
| | 0.7 | | | | | | |
| | 0.6 | | | | | | |
| | 0.5 | | | | | | |
| Total (Md) | 25.6 | 26.6 | 29.7 | 28.3 | 30.6 | 31.6 | 30.3 |

*There may be small fragments undetected on the gels which were run under the following conditions: 0.8% ME agarose (FMC), 3 mm thick gel (submarine) in Tris-acetate buffer (40 mM Tris, 12 mM Na acetate, 1 mM.Na$_2$EDTA, pH 7.8, with glacial acetic acid acid. Electrophoresis conditions at 5 volts/cm, 2.5 hours.

TABLE 2

| Enzyme | # Fragments | Fragment Sizes (kb) |
|---|---|---|
| BamHI | No cuts | — |
| KpnI | No cuts | — |
| PstI | No cuts | — |
| PvuI | No cuts | — |
| SalI | No cuts | — |
| SmaI | No cuts | — |
| PssI | 1 | 46.2 |
| SacI | 1 | 46.2 |
| XhoI | 1 | 46.2 |
| AatI | 2 | 39.5, 6.7 |
| AvaI | 2 | 24.5, 21.7 |
| BanII | 2 | 41.8, 4.4 |
| BglI | 2 | 24.9, 21.4 |
| BglII | 3 | 28.6, 13.5, 4.1 |
| HpaI | 3 | 27.7, 13.6, 4.1 |
| PvuII | 3 | 33.6, 7.6, 5.0 |
| ClaI | 5 | 15.0, 13.5, 8.2, 6.2, 3.8 |
| HaeIII | 5 | 28.6, 5.6, 5.2, 5.0, 1.1 |
| NcoI | 5 | 22.1, 18.9, 3.0, 1.8, 1.5 |
| EcoRI | 7 | 27.0, 10.3, 2.4, 2.1, 1.7, 1.1, 0.9 |
| HpaII | 7 | 12.7, 11.8, 10.6, 4.4, 2.7, 2.3, 0.9 |
| EcoRV | 8 | 24.0, 5.8, 4.7, 3.3, 2.7, 2.3, 1.4, 1.2 |
| HindIII | 16 | 7.3, 7.3, 5.0, 4.6, 3.3, 3.2, 3.0, 2.0, 1.8, 1.5, 1.4, 1.2, 1.2, 1.0, 0.9, 0.8 |
| HhaI | 18 | Not determined |
| AluI | many | Not determined |
| DraI | many | Not determined |

TABLE 3

Positions of Restriction Sites Mapped on pTR2030

| Enzyme | Map Position (kb) |
|---|---|
| AatI | 36.8, 43.5 |
| AvaI | 0/46.2, 24.5 |
| BanII | 40.8, 45.2 |
| BglI | 11.7, 33.0 |
| BglII | 2.6, 6.7, 35.2 |
| EcoRI | 0.5, 44.2 |
| HindIII | 42.1 |
| HpaII | 0.2 |
| PssI | 36.8 |
| PvuII | 32.7, 40.3, 45.3 |
| SacI | 45.2 |
| XhoI | 0/46.2 |

Plasmid pTR2030 exhibits conjugal transfer phenotypes of Tra+, Clu−, and phage resistance phenotypes of Hsp+, Hrp+. These phenotypes are described as follows:

Tra+: pTR2030 is a self-transmissable plasmid that promotes its own transfer and transfer of other non-conjugative plasmids. For example, pTR2030 is responsible for transfer of the non-conjugative plasmid pTR1040 (Lac+, Nis$^r$). In the absence of pTR2030, conjugation of pTR1040 does not occur. Consequently, pTR2030 can be used for mobilizing other plasmids in group N streptococci and possibly other gram-positive bacteria (i.e., S. faecalis, lactobacilli).

Clu−: pTR2030 exhibits high-frequency conjugal transfer in agar-surface matings. The frequency of conjugal transfer occurs at $10^{-1}$/donor cell in matings between S. lactis TRS1 (donor) and S. lactis LM2302 (recipient). pTR2030 does not induce the "clumping phenotype" (Clu+) in liquid media that has been observed previously for high-frequency conjugal plasmids of group N streptococci (Walsh, P. M. et al., J. Bacteriol. 146, 937 (1983); Anderson, D. G. et al., J. Bacteriol. 158, 954 (1984); Gasson, M. J. et al., J. Bacteriol. 143, 1260 (1980)). This Clu− phenotype is most desirable because the presence of this conjugal plasmid will not impose cell aggregation in transconjugants carrying pTR2030. Aggregating cultures are unsuitable for most applications in dairy and food fermentations.

The degree of phage resistance measured in different strains carrying pTR2030 varies, but herein is best described by two predominant phenotypes.

Hsp+: pTR2030 exhibits a heat-sensitive phage resistance property when present in S. lactis LM0230. Cells containing pTR2030 that are challenged with c2 phage at 30° C. form small plaques (~1 to 2 mm in diameter) at an efficiency of plaquing of 0.83. Normal plaque size for c2 phage on S. lactis LM0230 at 30° C. is 4 to 5 mm in diameter. When cells containing pTR2030 are propagated and challenged with c2 phage at 40° C., normal plaque sizes of 4 to 5 mm are observed. Plaque size was correlated with the burst size of phage and found dependent on the presence of pTR2030 and the temperature of the assay. pTR2030-imposed reduction in burst and plaque size occurs at 30° C., but not at 40° C.

Hrp+: pTR2030 exhibits a heat-resistant phage resistance property when present in S. cremoris strains HP, M43a, 924, KH, and TDM1. An Hrp+ property is exhibited in S. lactis LMA12 containing pTR2030 (Sanders, M. E. et al., Appl. Environ. Microbiol. 52, 1001 (1986). Lytic phages virulent for the parent S. cremoris strains (φhp, φm12r.M12, φ924, φkh, φ18, respectively) show no plaque formation (efficiency of plaquing (EOP) $< 10^{-9}$) on pTR2030 transconjugants under 30° C. or 40° C. incubation conditions. This Hrp+ phenotype represents the effective inhibition of plaquing of virulent phages on the S. cremoris and S. lactis transconjugants harboring pTR2030. The phage resistance of these transconjugants was temperature-independent.

Derivatives of pTR2030 include the following plasmids: (a) plasmid pTR2030 into which DNA sequences have been inserted; (b) plasmid pTR2030 from which DNA sequences have been deleted; (c) plasmid pTR2030 into which DNA sequences have been inserted and from which DNA sequences have been deleted; and (d) any plasmid into which a pTR2030 genetic determinant for phage resistance has been inserted. Additionally, a derivative of pTR2030 can include any plasmid into which any DNA sequence of pTR2030 has been inserted. It is preferred that each of these derivatives contain a pTR2030 genetic determinant for phage resistance. It is further preferred that each of these derivatives contain the pTR2030 genetic determinants for conjugal transfer. Examples of sequences which can be inserted into pTR2030 include host-specific promoters, enhancers or stronger promoters, DNA sequences which code for other types of phage resistance, DNA sequences for conjugal transfer, among others. Examples which can be deleted include any sequences which are not necessary for expression of phage resistance. For example, conjugal transfer coding sequences could be deleted. Additionally, any plasmid which is capable of replicating in Group N streptococci can be used for cloning the genetic determinants for phage resistance of pTR2030. A suitable plasmid can be prepared using a 13.5 kb fragment isolated from pTR2030 after cleavage with BglII.

The derivatives of pTR2030 can be prepared by using techniques well known in the art. Thus, insertions and/or deletions to pTR2030 can be performed using standard techniques. Many standard techniques have been described by Maniatis, T. et al., *Molecular Cloning: A Laboratory Manual*, Cold Spring Harbor Laboratory (1982). Similarly, pTR2030 genetic determinants for phage resistance (or any other pTR2030 DNA sequence) can be inserted into any plasmid using conventional techniques such as those described by Maniatis, T. et al., supra. A genetic determinant can be first isolated from pTR2030 and then inserted into a second plasmid. The second plasmid can be further tailored if necessary. A pTR2030 genetic determinant for phage resistance can be isolated as follows. Restriction fragments of pTR2030 are isolated and inserted into an appropriate plasmid vehicle for *S. cremoris* HP (ATCC No. 11602). The recombinant plasmid is then inserted into *S. cremoris* HP and the transformed bacteria analyzed for sensitivity to the phage φhp. Resistant colonies contain a plasmid carrying at least one of the pTR2030 genetic determinants for phage resistance. The restriction fragment with this determinant can be further manipulated as may be required, by using conventional techniques.

Suitable hosts for the plasmid pTR2030 or its derivatives are any microorganism in which pTR2030 or its derivatives are capable of replication. Preferred hosts are group N streptococci which include strains which are used in the production of cheese and cultured dairy products. Examples of these hosts are strains of *S. lactis, S. lactis* subsp. *diacetylactis*, and *S. cremoris*. Additional hosts include other gram-positive lactic acid bacteria which are used in dairy and food fermentations. Examples of these hosts include strains of Lactobacillus, Pediococcus and Leuconostoc. Plasmid pTR2030 or its derivatives can be introduced into any suitable host using standard techniques. Such techniques can include conjugal transfer as well as transformation.

Microorganisms containing pTR2030 or its derivatives exhibit resistance to phage. As a result of this property, the microorganisms with pTR2030 or its derivatives are extremely useful in the production of cheese and cultured dairy products as well as other food and dairy fermentations. The microorganisms are capable of more efficient fermentation since they are not sensitive to phages which are present or likely to appear in the fermentation vessel. Microorganisms containing pTR2030 or its derivatives are useful in formulation of starter cultures for the production of cheese and cultured dairy products. The preparation and use of starter cultures are well known in the art. Consequently, starter cultures can be formulated by using a microorganism containing pTR2030 or its derivatives in place of a microorganism currently employed. For example, a strain of *S. cremoris* carrying pTR2030 can be used in preparing a starter culture in place of the original strain of *S. cremoris* lacking pTR2030.

The present invention will be further described by reference to the following non-limiting examples.

EXAMPLE 1

Isolation of Plasmid pTR2030

*Streptococcus lactis* ME2 (conjugal donor, Lac+ Nis$^r$ Str$^s$) was mated with *Streptococcus lactis* LM0230 (plasmid-cured recipient, Lac$^-$ Nis$^s$ Str$^r$) on the surface of milk-glucose agar plates as described by McKay, L.L. et al., *Appl.Environ.Microbiol.* 40, 84 (1980). Donor and recipient cells were propagated for 4 hours at 30° C. in M17-lactose or M17-glucose broths, respectively. M17 broth was used as described by Terzaghi, B.E. et al., *Appl. Microbiol.* 29, 807 (1975). Lactose or glucose were present at 0.5% concentration. One part *S. lactis* ME2 cells was mixed with two parts *S. lactis* LM0230 cells and 0.2 ml of the suspension spread over the surface of a prepoured milk-glucose agar plate with a sterile glass rod. The plates were incubated for 18 hours at 30° C. Two ml of a broth containing 1% glucose and 5% nonfat dry milk solids were added to the surface of the plates and mixed with a sterile glass rod. One ml of this cell mixture was removed and 0.2 ml aliquots distributed over the surface of five selection plates containing lactose-indicator agar (McKay, L. L. et al., *Appl. Microbiol.* 23, 1090 (1972)) and 1 mg/ml streptomycin sulfate. The selection plates were incubated for 48 hours at 30° C. and examined for the appearance of yellow colonies. Recombinants were confirmed by phenotype and genotype as Lac+ Str$^r$ transconjugants. The frequency of Lac+ transfer from the donor to the recipient by conjugation was $2.8 \times 10^{-6}$/donor cell. All Lac+ transconjugants were scored for nisin resistance or sensitivity initially in Elliker broth or Elliker agar (1.5% w/v agar, pH 6.5) containing 0.1% (v/v) Tween 20 and 100 ng/ml nisin. Nisin stock solutions were prepared in 0.02M HCl as described by McKay, L. L. et al. (1984), supra, and were diluted to the desired concentration in 10% (w/v) Elliker broth. All Lac+ transconjugants were also Nis$^r$ and carried a 40 megadalton plasmid, pTR1040.

Lac+ Nis$^r$ Str$^r$ transconjugants generated from matings between *S. lactis* ME2 and *S. lactis* LM0230 were examined for sensitivity to lytic phage c2. Plaque assays were conducted as follows. Phage adsorption was measured as described by Sanders, M. E., et al., *Appl. Environ. Microbiol.* 40, 500 (1980). Phage assay, i.e., PFU/ml, was measured as described by Terzaghi, B. E. et al., supra. Burst size was measured as follows. Cells (1 ml) from 3.5 h cultures propagated at 30° C. or 40° C. were added to a sterile Eppendorf microfuge tube (1.5 ml). After centrifugation for 3 minutes the supernate was discarded, the pellets resuspended in 1 ml fresh M17-glucose broth and 50 µl 1 M-CaCl$_2$·7H$_2$O and 100 µl c2 phage ($10^8$–$10^9$ p.f.u./ml) were added. The broth was mixed gently and incubated for 5 minutes at 30° C. or 40° C. to allow for adsorption of phage. After centrifugation for 4 minutes, the supernate was aspirated and the cells resuspended in 1 ml M17-glucose broth plus calcium (50 µl 1 M-CaCl$_2$·7H$_2$O in 10 ml M17-glucose). This cell suspension was diluted to $10^{-4}$ in M17-glucose broth plus calcium. The diluted, phage-infected cell suspensions were incubated at 30° C. or 40° C. for 45 minutes. At 0 minutes and 45 minutes, 1 ml samples were removed and immediately subjected to plaque assay without treatment with chloroform. Burst size was calculated as the number of progeny phage at 45 minutes divided by the total number of infective centers at time 0. In such assays, 4% of the transconjugants exhibited plaques that were significantly smaller than those observed for phage c2 on the conjugal recipient, S. lactis LM0230. Burst size of c2 phage on the transconjugants at 30° C. was reduced to 5 phage per cell, as compared to a burst size of 41 for c2 phage on the recipient, S. lactis LM0230. A 30 megadalton plasmid, designated pTR2030, was found to be responsible for the phage-resistance exhibited by these Lac+ Nis$^r$ transconjugants selected from matings between S. lactis ME2 and S. lactis LM0230. The resistance to c2 phage, imposed by pTR2030 in S. lactis LM0230, was defined as the Hsp+ phenotype. One of these transconjugants, S. lactis TRS1, harbors both pTR1040 and pTR2030. Following growth of S. lactis TRS1 at 40° C., a Lac− Nis$^s$ derivative was isolated. This isolate exhibits Hsp+, carries a 30±3.0 megadalton plasmid (pTR2030), and was designated S. lactis TRS1-a (phenotype Hsp+, Str$^r$, Lac−). TRS1-a containing pTR2030 was deposited on Jun. 10, 1985 under the Budapest Treaty at the American Type Culture Collection, and has been assigned number 53,146.

Plasmid pTR2030 was isolated from S. lactis TRS1-a by the method of Klaenhammer, T. R., Current Microbiol. 10, 23 (1984) using the modifications described by Sanders, M. E. et al. (1983), supra. Restriction endonucleases were obtained from Bethesda Research Laboratories and restriction digestions were performed using the method of Maniatis, T. et al., supra. Separation of DNA restriction fragments were accomplished on 0.8% agarose gels. Fragments generated by HindIII and EcoRI digestions of λ DNA served as molecular weight standards. The results of restriction enzyme digestion are shown in Tables 1 amd 2, supra. The map positions of restriction sites are shown in Table 3, supra, and in FIG. 1.

EXAMPLE 2

Preparation of S. lactis TEK1

For use in conjugation experiments to Str$^r$ recipients of S. cremoris, a Str$^s$ donor strain which carried pTR1040 (Lac+ Nis$^r$) and pTR2030 (Hsp+ Tra+) was developed. Matings were conducted between S. lactis TRS1 and S. lactis C14$_5$ (plasmid-cured, Lac− Hsp− Str$^s$) as described above in Example 1. Lac+ colonies were selected on lactose-indicator agar without added streptomycin. 100 Lac+ colonies were examined for Hsp+ and sensitivity to streptomycin. S. lactis TEK1 was detected as a Lac+ Hsp+ Str$^s$ transconjugant which carried pTR1040 and pTR2030. This culture was used as the donor of pTR2030 in conjugation experiments with S. cremoris Str$^r$ recipients as described further below. S. lactis TEK1 containing pTR2030 and pTR1040 was deposited on Jun. 25, 1985 under the Budapest Treaty at the American Type Culture Collection, and has been assigned number 53,167.

EXAMPLE 3

Preparation of S. cremoris M43a

For use as conjugation recipients, Lac− variants of S. cremoris M12R were isolated on lactose-indicator agar following 24 hours of growth in M17-glucose broth containing 2 μg/ml ethidium bromide. Lac− variant M43 was purified by single colony isolation on lactose-indicator agar, propagated through M17-glucose broth, and 0.1 ml spread over the surface of M17-glucose agar plates containing 250, 500, and 1,000 μg/ml streptomycin sulfate. After 24 to 48 hours at 30° C., single colonies appearing on plates with the highest concentration of streptomycin were picked and streaked onto M17-glucose agar containing 1 mg/ml streptomycin. One streptomycin-resistant (Str$^r$) variant was selected in this manner and designated M43a. The identity of the Lac− Str$^r$ variant was confirmed by plasmid composition and sensitivity to the S. cremoris M12R lytic phage (m12r·M12) in standard plaque assays as described in Example 1. S. cremoris M43a was maintained in M17-glucose broth and 1 mg/ml streptomycin, but was propagated once in the absence of streptomycin before use in conjugation experiments.

EXAMPLE 4

Conjugal Transfer of pTR1040 and pTR2030

Matings were conducted between S. lactis ME2 as the donor strain and S. lactis LM0230 and S. cremoris M43a as the recipient strains, as described in Example 1. Lac+ colonies were selected on lactose-indicator agar and 1 mg/ml streptomycin sulfate as described in Example 1. Nisin resistance was examined as described in Example 1, except that 50 ng/ml of nisin was used instead of 100 ng/ml. Phage resistance was determined by the procedure described in Example 1. Phage resistance in the LM0230 Lac+ transconjugants was measured as Hsp+, a reduction in plaque and burst size for c2 phage. Phage resistance in the S. cremoris M43a Lac+ transconjugants was measured as Hrp+, no plaque formation (EOP<4.3×10$^{-10}$) by phage m12r.M12 (see S. cremoris T2r-M43a, Example 5, Table 5). The results of the conjugation experiment are shown in Table 4. Samples of either ME2 or LM0230 alone gave no recombinants. Frequency was less than 7.6×10$^{-9}$ recombinants/donor.

TABLE 4

| | Lac+ Str$^r$ Recombinants | | | |
|---|---|---|---|---|
| Recipient | per ml | frequency/ donor | % nisin resistant | % phage resistant |
| S. lactis LM0230 | 369 | 2.8 × 10$^{-6}$ | 100 | 4 |
| S. cremoris M43a | 19,010 | 1.1 × 10$^{-4}$ | 100 | 57 |

EXAMPLE 5

Hsp+ and Hrp+ Phenotypes in pTR2030 Transconjugants

One of the transconjugants of S. lactis LM0230 and S. lactis ME2 produced in Example 1 was sensitive to phage c2. This transconjugant was identified as S. lactis TRS3 and was found to contain only plasmid pTR1040 and not pTR2030. Matings were conducted between S. lactis ME2 and S. cremoris M43a and examined as described in Example 1. One of the transconjugants was Lac+ Nis$^r$, which was phage resistant and was found to contain both pTR1040 and pTR2030. This transconjugant was identified as S. cremoris T2r-M43a. A second transconjugant which was phage sensitive was found to contain only pTR1040 and not pTR2030. This second transconjugant was identified as S. cremoris T2s-M43a.

The adsorption, burst size and efficiency of plaquing (EOP) of phage on S. lactis strains LM0230, TRS1 and TRS3, and on S. cremoris strains M43a, T2s-M43a and T2r-M43a were determined using phage c2 and m12r·M12, respectively, as described in Example 1. The results are shown in Table 5.

Phage resistance was detected only in those transconjugants carrying pTR2030. pTR2030 in the S. lactis transconjugant TRS1 exhibited Hsp+. pTR2030 in the S. cremoris transconjugant T2r-M43a exhibited Hrp+. The phage resistance imposed by the presence of pTR2030 in different bacterial hosts is variable and can be described phenotypically as Hsp+ or Hrp+.

TABLE 5

| Strain | Plasmids | Phenotype | % Adsorption Phage | EOP | Burst Size at 30° C. | Burst Size at 40° C. |
| --- | --- | --- | --- | --- | --- | --- |
| S. lactis | | | | | | |
| LM0230 | — | Lac⁻Nis$^s$Hsp⁻ | 99% | 1.0 | 40 | 56 |
| TRS3 | pTR1040 | Lac⁺Nis$^r$Hsp⁻ | 96% | 1.0 | 41 | 66 |
| TRS1 | pTR1040 pTR2030 | Lac⁺Nis$^r$Hsp⁺ | 98% | 0.83 | 5 | 51 |
| S. cremoris | | | | | | |
| M43a | — | Lac⁻Nis$^s$Hrp⁻ | 99% | 1.0 | NA | NA |
| T2s-M43a | pTR1040 | Lac⁺Nis$^r$Hrp⁻ | ND | 1.1 | NA | NA |
| T2r-M43a | pTR1040 pTR2030 | Lac⁺Nis$^r$Hrp⁺ | 98% | $<4.3 \times 10^{-10}$ | NA | NA |

NA = not applicable
ND = not determined

EXAMPLE 6

Demonstration of Tra+ of pTR2030

Matings were conducted between various donor strains identified in Table 5 and a recipient strain S. lactis LM2302 (Lac⁻ Nis$^s$ Ery$^r$ Str$^r$), and transconjugants were selected on lactose-indicator agar containing 15 μg/ml erythromycin and 1 mg/ml streptomycin as described in Example 1. The results shown in Table 6 demonstrate that pTR2030 promotes high-frequency transfer of Hsp+/Hrp+ (found on pTR2030) and Lac+ and Nis$^r$ encoded by plasmid pTR1040. pTR1040 is not self-transmissible and is not conjugally transferred in the absence of pTR2030.

TABLE 6

| Donor | Plasmids | Phenotype of Donor | Lac⁺Nis$^r$Ery$^r$Str$^r$ recombinants Per ml | Freq./donor | % Hsp⁺/Hrp⁺ |
| --- | --- | --- | --- | --- | --- |
| TRS1 | pTR1040 pTR2030 | Lac⁺Nis$^r$Hsp⁺ | $9.6 \times 10^6$ | $1.2 \times 10^{-1}$ | 85% |
| TRS3 | pTR1040 | Lac⁺Nis$^r$Hsp⁻ | 0 | $<3.8 \times 10^{-10}$ | 0% |
| T2r-M43a | pTR1040 pTR2030 | Lac⁺Nis$^r$Hrp⁺ | $1.7 \times 10^6$ | $2.6 \times 10^{-2}$ | 67% |
| T2s-M43a | pTR1040 | Lac⁺Nis$^r$Hrp⁻ | 0 | $<5.2 \times 10^{-8}$ | 0% |

EXAMPLE 7

Conjugal transfer of pTR2030 to strains of S. cremoris

Matings were conducted between donor strains (Lac+ Nis$^r$ Str⁻ Tra+ Hsp+) and recipient strains (Lac⁻ Nis$^s$ Str$^r$) of S. cremoris as shown in Table 5, and transconjugants were selected as described in Example 1. Phage-resistant transconjugants were Hrp+ and confirmed to carry pTR2030. The results are shown in Table 7. It can be seen that pTR2030 can be conjugally transferred between these strains.

TABLE 7

| Mating Pair | | Lac⁺ Str$^r$ Transconjugants | |
| --- | --- | --- | --- |
| Donor S. lactis | Recipient S. cremoris | Freq./Donor | % Phage Resistant (Hrp⁺) |
| TEK1 | M43a | $3.3 \times 10^{-2}$ | 27% |
| TEK1 | KHA2 | $4.5 \times 10^{-6}$ | 25% |
| TEK1 | HPA4 | $4.0 \times 10^{-4}$ | 20% |
| TEK1 | 924EB1 | $1.1 \times 10^{-4}$ | 28% |
| ME2 | TDM1R3 | $6.9 \times 10^{-5}$ | 62% |

EXAMPLE 8

Effect of Phage on S. cremoris Transconjugants

Plaque assays with various S. cremoris strains were determined as described in Example 1. The results are shown in Table 8. It can be seen that four different S. cremoris strains containing pTR2030 were Hrp+. Phages failed to form plaques (EOP$<10^{-9}$) on the pTR2030 transconjugants.

TABLE 8

| Strain | Description | Phage | PFU/ml* | EOP |
| --- | --- | --- | --- | --- |
| M43a | phage sensitive parent | m12r·M12 | $1.4 \times 10^{10}$ | 1.0 |
| T2r-M43a | pTR2030 trans-conjugant | m12r·M12 | <10 | $<7.1 \times 10^{-10}$ |
| KH | phage sensitive parent | φkh | $5.6 \times 10^9$ | 1.0 |
| TKH1 | pTR2030 trans-conjugant | φkh | <10 | $<1.8 \times 10^{-9}$ |
| HP | phage sensitive parent | φhp | $6.7 \times 10^9$ | 1.0 |
| THP14 | pTR2030 trans-conjugant | φhp | <10 | $<1.5 \times 10^{-9}$ |
| 924 | phage sensitive parent | φ924 | $1.9 \times 10^9$ | 1.0 |

TABLE 8-continued

| Strain | Description | Phage | PFU/ml* | EOP |
|---|---|---|---|---|
| T9249 | pTR2030 transconjugant | φ924 | <10 | <5.3 × $10^{-9}$ |
| TDM1 | phage sensitive parent | φ18 | 3.6 × $10^{10}$ | 1.0 |
| TM-TDM1R3 | pTR2030 transconjugant | φ18 | <10 | <2.8 × $10^{-9}$ |

*Plaque forming units/ml of phage suspension

EXAMPLE 9

Effect of Phages on S. cremoris M12 and M43a

Virulent phages were independently isolated from cheese plants using a starter culture comprising S. cremoris M12 cells. Plaque assays with S. cremoris M12 and S. cremoris T2r-M43a were determined as described in Example 1. The results are shown in Table 9, where it can be seen that the transconjugant containing pTR2030, i.e., S. cremoris T2r-M43a, was resistant to all phages tested (i.e., the phages failed to replicate on this strain).

TABLE 9

| | M12 | | T2r-M43a | |
|---|---|---|---|---|
| Phage | Titer, PFU/Ml | EOP | Titer, PFU/ml | EOP |
| m12r · M12 | 2.8 × $10^{10}$ | 1.0 | <10 | <3.6 × $10^{-10}$ |
| φ05 | 3.8 × $10^{10}$ | 1.0 | <10 | <2.7 × $10^{-10}$ |
| da | 4.6 × $10^9$ | 1.0 | <10 | <2.2 × $10^{-9}$ |
| br | 5.8 × $10^9$ | 1.0 | <10 | <1.7 × $10^{-9}$ |
| ot | 1.9 × $10^{10}$ | 1.0 | <10 | <5.3 × $10^{-10}$ |
| sgl | 3.2 × $10^{10}$ | 1.0 | <10 | <3.1 × $10^{-10}$ |

EXAMPLE 10

Starter Culture Activity Test

The starter culture activity test was a modification of that described by Heap, H. A. et al., N.Z.J. Dairy Sci. Technol. 11, 16 (1976). Cultures were prepared by overnight incubation at 30° C. in 11% reconstituted skim milk (RSM, steamed for one hour); or in 11% RSM containing 0.25% casamino acids (RSM/CA) for growth of proteinase-negative strains (for M43a and T2r-M43a only). Phage suspension (200 μl, ~$10^8$ PFU/ml) was mixed with 200 μl of milk culture and incubated at room temperature for 10 minutes to allow adsorption of phage. RSM or RSM/CA (9.6 ml) containing 40 μg/ml bromocresol purple (BCP) was added and the tubes were sequentially incubated for 180 minutes at 30° C., 190 minutes at 40° C., and 150 minutes at 30° C. for S. cremoris M43 and T2r-M43a, and 100 minutes at 30° C., 190 minutes at 40° C. and 100 minutes at 30° C. for all other strains. Following the incubation, milk samples were examined for pH and phage titer. The initial pH of the milk was 6.5-6.6. The results given in Table 10 show that virulent phages failed to replicate on strains of S. cremoris which contained pTR2030 and the phages did not inhibit acid development during the starter culture activity test. The starter culture activity test demonstrates that phage resistance imposed by pTR2030 was effective under fermentation and temperature conditions encountered in commercial cheesemaking. All the S. cremoris transconjugants displayed Hrp+; complete resistance to phage that is temperature independent.

TABLE 10

| Strain | Description | Phage | Phage Titer (PFU/ml) Initial | Phage Titer (PFU/ml) Final | Final pH |
|---|---|---|---|---|---|
| S. cremoris M43 | Lac+ parent | — | — | — | 5.9 |
| | | +m12r · M12 | 4.1 × $10^6$ | 5.2 × $10^9$ | 6.5 |
| S. cremoris T2r-M43a | pTR2030 transconjugant | — | — | — | 5.9 |
| | | +m12r · M12 | 4.1 × $10^6$ | 2.7 × $10^3$ | 5.9 |
| S. cremoris KH | Lac+ parent | — | — | — | 5.6 |
| | | +φkh | 3.0 × $10^6$ | 1.3 × $10^{10}$ | 6.4 |
| S. cremoris TKH1 | pTR2030 transconjugant | — | — | — | 5.4 |
| | | +φkh | 3.0 × $10^6$ | 4.0 × $10^3$ | 5.4 |
| S. cremoris HP | Lac+ parent | — | — | — | 5.8 |
| | | +φhp | 3.1 × $10^6$ | 4.9 × $10^9$ | 6.4 |
| S. cremoris THP14 | pTR2030 transconjugant | — | — | — | 5.8 |
| | | +φhp | 3.1 × $10^6$ | 1.9 × $10^3$ | 5.9 |
| S. cremoris 924 | Lac+ parent | — | — | — | 5.7 |
| | | +φ924 | 6.7 × $10^5$ | 1.8 × $10^8$ | 6.0 |
| S. cremoris T9249 | pTR2030 transconjugant | — | — | — | 5.8 |
| | | +φ924 | 6.7 × $10^5$ | 9.5 × $10^4$ | 5.8 |
| S. cremoris TDM1 | Lac+ parent | — | — | — | 4.9 |
| | | +φ18 | 5.2 × $10^6$ | 3.0 × $10^9$ | 6.4 |
| S. cremoris TM-TDM1R3 | pTR2030 transconjugant | — | — | — | 5.1 |
| | | +φ18 | 5.2 × $10^6$ | 7.0 × $10^6$ | 5.1 |

A consecutive starter culture activity test was conducted using m12r·M12 phage to determine whether or not virulent phage could be generated which was active against the S. cremoris T2r-M43a transconjugant. Repeated cycles of the activity test were conducted as above except that 100 μl of m12r·M12 phage suspension (~$10^8$ PFU/ml, prepared in M17 broth) and 100 μl of whey collected from the previous activity test were mixed with 200 μl of cells prior to milk inoculation. It was found that virulent phage also failed to develop toward S. cremoris T2r-M43a which contained pTR2030 in the consecutive starter culture activity test.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

What is claimed is:

1. A starter culture for fermenting milk comprising a group N Streptococcus containing and capable of replicating the plasmid pTR2030, the plasmid pTR2030 characterized by a molecular weight of 30.0±3.0 megadaltons, having the following sensitivity to restriction endonucleases:

| Enzyme | # sites |
|--------|---------|
| HindIII | 16 |
| HaeIII | 4 |
| EcoRI | 8 |
| XbaI | 5 |
| HpaI | 3 |
| NcoI | 5 |
| AvaI | 2 | which plasmid encodes for phage resistance phenotype and conjugal transfer phenotype upon expression in group N Streptococci.

2. The starter culture of claim 1, wherein said group N Streptococcus is selected from the group consisting of S. lactis, S. lactis subsp. diacetylactis and S. cremoris.

3. A starter culture for fermenting milk comprising a group N Streptococcus containing and capable of replicating a plasmid comprising a derivative of pTR2030, the plasmid pTR2030 encoding a phage resistance phenotype and conjugal transfer phenotype upon expression in group N streptococci, said derivative encoding the phage resistance phenotype encoded for by the plasmid pTR2030 upon expression in Group N streptococci.

4. The starter culture of claim 3, said derivative further encoding the conjugal transfer phenotype encoded for by the plasmid pTR2030 upon expression in Group N streptococci.

5. The starter culture of claim 4, wherein said group N Streptococcus is selected from the group consisting of S. lactis, S. lactis subsp. diacetylactis and S. cremoris.

6. The starter culture of claim 3, wherein said group N Streptococcus is selected from the group consisting of S. lactis, S. lactis subsp. diacetylactis and S. cremoris.

* * * * *

UNITED STATES PATENT AND TRADEMARK OFFICE
CERTIFICATE OF CORRECTION

PATENT NO.   : 5,139,950

DATED        : August 18, 1992

INVENTOR(S)  : Todd R. Klaenhammer, Rosemary B. Sanozky, Larry R. Steenson, and Wesley D. Sing It is certified that error appears in the above-identified patent and that said Letters Patent is hereby corrected as shown below:

On the Title page, item [75],

Inventor, Wesley D. Sing, of Raleigh, North Carolina missing from Patent.

Signed and Sealed this

Seventeenth Day of August, 1993

Attest:

BRUCE LEHMAN

*Attesting Officer*      *Commissioner of Patents and Trademarks*